(12) United States Patent
Suzuki et al.

(10) Patent No.: US 7,129,367 B2
(45) Date of Patent: Oct. 31, 2006

(54) PHOSPHINE COMPOUND, ITS INTERMEDIATE, ITS COMPLEX WITH PALLADIUM AND A MANUFACTURING METHOD OF UNSATURATED COMPOUNDS BY USING THE PALLADIUM COMPLEX

(75) Inventors: Ken Suzuki, Hiratsuka (JP); Yoji Hori, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 10/542,941

(22) PCT Filed: Feb. 12, 2004

(86) PCT No.: PCT/JP2004/001514

§ 371 (c)(1),
(2), (4) Date: Jul. 21, 2005

(87) PCT Pub. No.: WO2004/072088

PCT Pub. Date: Aug. 26, 2004

(65) Prior Publication Data

US 2006/0058542 A1 Mar. 16, 2006

(30) Foreign Application Priority Data

Feb. 14, 2003 (JP) ............................. 2003-037399

(51) Int. Cl.
| C07F 15/00 | (2006.01) |
| C07F 9/02 | (2006.01) |
| C07C 69/76 | (2006.01) |
| C07C 45/00 | (2006.01) |
| C07C 253/00 | (2006.01) |
| B01J 31/00 | (2006.01) |

(52) U.S. Cl. ............................. 556/21; 585/25; 568/8; 568/15; 568/319; 568/323; 502/162; 560/51; 560/54

(58) Field of Classification Search .................. 556/21; 568/8, 15, 319, 323; 585/25; 502/162; 560/51, 560/54; 558/342
See application file for complete search history.

(56) References Cited

OTHER PUBLICATIONS

M. Topolski et al., "Chiral Carbenoids: Their Formation and Reactions", Journal of Organic Chemistry, vol. 58, No. 3, pp. 546-555, 1993.
H. M. Walborsky et al., "Carbenoids. Metal Assisted Ionization", Tetrahedron Letters, vol. 26, No. 23, pp. 2743-2746, 1985.
G. Boche et al., "Alternative Pathways in the Reactions of Cyclopropyl Halides with Alkali Metal Naphthalenes", Journal of the American Chemical Society, vol. 102, No. 17, pp. 5697-5699, 1980.
R. Luckenbach et al., "Electrocyclic Ring Opening of Cyclopropyl Halides in the Course of their Reactions with Sodium Iodide in Acetone", Zeit. Fuer Natur., vol. 34B, No. 3, pp. 464-480, 1979.

V. Sander et al., "Synthesis and Reactions of 1-Chloro-1-cyclopropanecarboxylic Acids and 1-Cyclopropene-1-carboxylic Acids", Chem. Ber., vol. 111, No. 12, pp. 3879-3891, 1978.
H. M. Walborsky et al., "Cyclopropanes. XXXIII. Reaction of Lithium Metal Surfaces with Optically Active 1-halo-1-Methyl-2,2-Diphenylcyclopropane", Journal of Organometallic Chemistry, vol. 51, pp. 55-75, 1973.
H. M. Walborsky et al., "Cyclopropanes. XXXII. The Mechanism of Grignard Formation", Journal of Organometallic Chemistry, vol. 51, pp. 31-53, 1973.
H. M. Walborsky et al., "Cyclopropanes, XXIX. The Sterochemistry of the 1-Methyl-2,2-diphenylcyclopropyl Radical in and out of Solvent Cage", Journal of the American Chemical Society, vol. 93, No. 3, pp. 671-675, 1971.
J. W. Hausser et al., "Solvolysis of Cyclopropyl Halides. 2-Phenylcyclopropyl Chlorides[1,2]", Journal of the American Chemical Society, vol. 89, No. 26, pp. 6981-6984, 1967.
H. Ikeda et al., "Spectroscopic and Calorimetric Studies on the Mechanism of Methylenecyclopropane Rearrangements Triggered by Photoinduced Election Transfer", Journal of the American Chemical Society, vol. 125, No. 30, pp. 9147-9157, 2003.

*Primary Examiner*—Porfirio Nazario-Gonzalez
(74) *Attorney, Agent, or Firm*—Wenderoth, Lind & Ponack, L.L.P.

(57) ABSTRACT

Palladum-phosphine complexes obtained by reacting a 5 compound of formula (1) below with a palladium compound: F(I) (wherein $R^1$ is a hydrogen atom, an alkyl group, a cycloalkyl group or a phenyl group which may be substituted; $R^2$ and $R^3$ are each, the same or different, an alkyl group, a cycloalkyl group or a phenyl group which may be substituted; $R^4$ and $R^5$ are each, the same or different, a hydrogen atom, an alkyl group, a cycloalkyl group or a phenyl group which may be substituted; $R^6$, $R^7$, $R^8$ and $R^9$ are each, the same or different, an alkyl group, a cycloalkyl group, a phenyl group which may be substituted, an alkoxyl group, a dialkylamino group, a halogen atom, a phenyl group, a benzyl group, a naphthyl group or a halogenated alkyl group; $R^6$ and $R^7$, $R^8$ and $R^9$ may be combined to form, each, a fused ring, a trimethylene group, a tetramethylene group or a 20 methylenedioxy group; p, q, r and s are each an integer of 0 to 5; and p+q, and r+s are each in the range of 0 to 5.), which is a novel and efficient catalyst for manufacturing various useful compounds (1)

12 Claims, No Drawings

1

PHOSPHINE COMPOUND, ITS INTERMEDIATE, ITS COMPLEX WITH PALLADIUM AND A MANUFACTURING METHOD OF UNSATURATED COMPOUNDS BY USING THE PALLADIUM COMPLEX

This application is a U.S. national stage of International Application No. PCT/JP2004/001514 filed Feb. 12, 2004.

TECHNICAL FIELD

The present invention relates to a phosphine compound, its intermediate, and a palladium-phosphine complex obtainable by treating the said phosphine compound with a palladium compound. The present invention also relates to a manufacturing method of unsaturated compounds or aromatic compounds by using the said palladium-phosphine complex as a catalyst.

BACKGROUND ART

At present many transition metal complexes have been used as catalysts for organic synthetic reactions. It is well known that the ligand plays a very important role, together with the transition metals as the central metals, as a factor to make full use of the performance or activity of those catalysts. Many phosphine compounds, for example, have been developed as the ligands and have had a key role as such.

The most important thing is to constitute an optimal catalyst for each of the various kinds of reactions and substrates. However, the combination of the central metal and the phosphine ligand, constituting the catalyst, is so complex that the known phosphine ligands may, in some cases, be insufficient without, for example, yielding enough catalytic activity for use in the practical industrial production. Thus, development of excellent novel phosphine ligands is still eagerly desired.

DISCLOSURE OF INVENTION

Accordingly, the object of the present invention is to provide a novel ligand useful for various catalytic reactions and to provide, furthermore, by using the catalysts which contain this ligand, a method for manufacturing unsaturated compounds which are important as intermediates of pharmaceuticals and organic electronic materials.

The present inventors have found, after an intensive study to solve the problem mentioned above, that a novel phosphine compound with a cyclopropane moiety is an excellent ligand and that the complex of this novel phosphine compound with a palladium compound is extremely efficient as catalyst for the synthesis of unsaturated or aromatic compounds, making it possible to manufacture efficiently unsaturated or aromatic compounds, particularly aromatic compounds, and completed the present invention. Furthermore, the present inventors have also found a novel intermediate for manufacturing the phosphine compound with a cyclopropane skeleton mentioned above.

Thus the present invention includes the following:
1. a phosphine compound of formula (1),

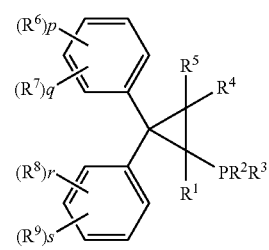

(1)

wherein $R^1$ is a hydrogen atom, an alkyl group, a cycloalkyl group or a phenyl group which may be substituted; $R^2$ and $R^3$ are each, the same or different, an alkyl group, a cycloalkyl group or a phenyl group which may be substituted; $R^4$ and $R^5$ are each, the same or different, a hydrogen atom, an alkyl group, a cycloalkyl group or a phenyl group which may be substituted; $R^6$, $R^7$, $R^8$ and $R^9$ are each, the same or different, an alkyl group, a cycloalkyl group, a phenyl group which may be substituted, an alkoxyl group, a dialkylamino group, a halogen atom, a benzyl group, a naphthyl group or a halogenated alkyl group; $R^6$ and $R^7$, or $R^8$ and $R^9$ each may be combined to form, a fused ring, a trimethylene group, a tetramethylene group or a methylenedioxy group; p, q, r and s are each an integer of from 0 to 5; and p+q, and r+s are each in the range of from 0 to 5;

2. a palladium-phosphine complex which can be obtained by reacting the phosphine compound mentioned in 1 above with a palladium compound;

3. the palladium-phosphine complex mentioned in 2 above, wherein the palladium compound is a palladium salt or a palladium complex in which the valency of palladium is 4, 2 or 0;

4. a manufacturing method of an unsaturated compound or an aromatic compound by the use of palladium-phosphine complexes mentioned in 2 or 3 above as a catalyst;

5. a manufacturing method of an unsaturated compound or an aromatic compound by the use of the phosphine compound mentioned in 1 above and a palladium compound.

6. the manufacturing method mentioned in 4 or 5 above, which comprises reacting a compound of formula (3) or (4) below,

(3)

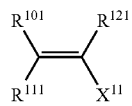

(4)

wherein, in formula (3), $Ar^1$ is an aryl group which may be substituted or a heteroaryl group which may be substituted; $X^1$ is a chlorine atom, a bromine atom, an iodine atom, a trifluoromethanesulfonyloxy group, a methanesulfonyloxy group or a para-toluenesulfonyloxy group and $m^1$ is an integer of from 1 to 4, and, in formula (4), $R^{101}$, $R^{111}$ and $R^{121}$ are each, the same or different, a hydrogen atom, an alkyl group, an aryl group which may be substituted, a heteroaryl group which may be substituted, an alkoxycarbonyl group or a cyano group; $X^{11}$ is a chlorine atom, a bromine atom, an iodine atom, a trifluoromethanesulfonyloxy group, a methanesulfonyloxy group or a para-toluenesulfonyloxy group, with a compound, of formula (5) or (6) below, $$Ar^2X^2 \quad (5)$$

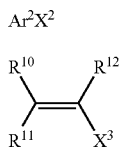
(6)

wherein, in formula (5), $Ar^2$ is an aryl group which may be substituted or a heteroaryl group which may be substituted; $X^2$ is $B(OR^{13})(OR^{14})$, $Sn(R^{15})_3$, MgX, ZnX, $Al(R^{15})_2$ or Li, and, in formula (6), $R^{10}$, $R^{11}$ and $R^{12}$ are each, the same or different, a hydrogen atom, an alkyl group, an aryl group which may be substituted, a heteroaryl group which may be substituted, an alkoxycarbonyl group or a cyano group; $R^{10}$ and $R^{12}$ may be combined to form a single bond, forming together with the existing double bond a triple bond; $X^3$ is a hydrogen atom, $B(OR^{13})(OR^{14})$, $Sn(R^{15})_3$, MgX, ZnX, $Al(R^{15})_2$ or Li; $R^{13}$ and $R^{14}$ are each, the same or different, a hydrogen atom, an alkyl group, or, combined to form an ethylene group or a 1,2-dimethylethylene group; $R^{15}$ is an alkyl group, and X is a chlorine atom, a bromine atom or an iodine atom, to give a compound of formula (7), (8), (9) or (10), $$Ar^1 \!-\! (Ar^2)m^2 \quad (7)$$

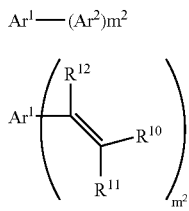
(8)

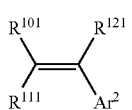
(9)

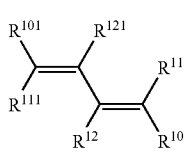
(10)

wherein $Ar^1$, $Ar^2$, $R^{10}$, $R^{11}$, $R^{12}$, $R^{101}$, $R^{111}$ and $R^{121}$ are as defined above and $m^2$ is an integer of 1 to 4;

7. a manufacturing method mentioned in 4 or 5 above, which comprises reacting a compound of formula (3) or (4) below, $$Ar^1(X^1)m^1 \quad (3)$$

(4)

wherein, in formula (3), $Ar^1$ is an aryl group which may be substituted or a heteroaryl group which may be substituted; $X^1$ is a chlorine atom, a bromine atom, an iodine atom, a trifluoromethanesulfonyloxy group, a methanesulfonyloxy group or a para-toluenesulfonyloxy group and $m^1$ is an integer of from 1 to 4, and, in formula (4), $R^{101}$, $R^{111}$ and $R^{121}$ are each, the same or different, a hydrogen atom, an alkyl group, an aryl group which may be substituted, a heteroaryl group which may be substituted, an alkoxycarbonyl group or a cyano group; $X^{11}$ is a chlorine atom, a bromine atom, an iodine atom, a trifluoromethanesulfonyloxy group, a methanesulfonyloxy group or a para-toluenesulfonyloxy group, with an oxygen compound or nitrogen compound of formula (11) below, $$R^{16}\text{-QH} \quad (11)$$

wherein $R^{16}$ is an alkyl group, an aryl group which may be substituted, or a heteroaryl group which may be substituted; Q is an oxygen atom,

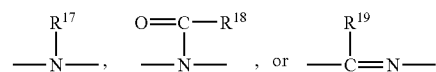

wherein $R^{17}$, $R^{18}$ and $R^{19}$ are each a hydrogen atom, an alkyl group, an aryl group which may be substituted or a heteroaryl group which may be substituted; and $R^{16}$ and $R^{17}$ may be combined to form a divalent aromatic ring which may be substituted, to give a compound of formula (12) or (13) below, $$Ar^1(QR^{16})m^3 \quad (12)$$

(13)

wherein $Ar^1$, Q, $R^{16}$, $R^{101}$, $R^{111}$, and $R^{121}$ are as defined above and $m^3$ is an integer of 1 to 4.

8. the manufacturing method mentioned in 4 or 5 above, which comprises reacting an aromatic compound of formula (3),

wherein $Ar^1$ is an aryl group which may be substituted or a heteroaryl group which may be substituted; $X^1$ is a chlorine atom, a bromine atom, an iodine atom, a trifluoromethanesulfonyloxy group, a methanesulfonyloxy group or a para-toluenesulfonyloxy group, and $m^1$ is an integer of from 1 to 4, with a carbonyl compound or a cyano compound of formula (14),

$$R^{18}-CH_2-R^{19} \tag{14}$$

wherein $R^{18}$ is a hydrogen atom, $CO_2R^{20}$, $C(=O)R^{21}$ or a cyano group; $R^{19}$ is $CO_2R^{22}$, $C(=O)R^{23}$ or a cyano group; $R^{20}$, $R^{21}$, $R^{22}$ and $R^{23}$ are each an alkyl group, an aryl group which may be substituted or a heteroaryl group which may be substituted, to give a compound of formula (15),

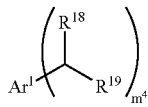
$$\left( Ar^1 \underset{R^{19}}{\overset{R^{18}}{\diagup}} \right)_{m^4} \tag{15}$$

wherein $Ar^1$, $R^{18}$ and $R^{19}$ are as defined above and $m^4$ is an integer of 1 to 4.

9. the manufacturing method mentioned in 4 or 5 above, which comprises reacting an aromatic compound of formula (3),

$$Ar^1(X^1)_{m^1} \tag{3}$$

wherein $Ar^1$ is an aryl group which may be substituted or a heteroaryl group which may be substituted; $X^1$ is a chlorine atom, a bromine atom, an iodine atom, a trifluoromethanesulfonyloxy group, a methanesulfonyloxy group or a paratoluenesulfonyloxy group; and $m^1$ is an integer of from 1 to 4, with carbon monoxide and an alcohol of formula (16),

$$R^{24}OH \tag{16}$$

wherein $R^{24}$ is an alkyl group, to give a carboxylic ester of formula (17),

$$Ar^1(CO_2R^{24})_{m^5} \tag{17}$$

wherein $Ar^1$ and $R^{24}$ are as defined above and $m^5$ is an integer of 1 to 4.

10. the manufacturing method of unsaturated compounds mentioned in any one of 4 to 9 above, which comprises carrying out the reaction in the presence of a base;

11. a halogeno compound of formula (2) below,

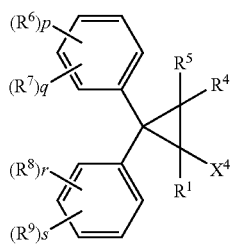
$$(2)$$

wherein $R^1$, $R^4$ and $R^5$ are each, the same or different, a hydrogen atom, an alkyl group, a cycloalkyl group or a phenyl group which may be substituted; $X^4$ is a halogen atom; $R^6$, $R^7$, $R^8$ and $R^9$ are each, the same or different, an alkyl group, a cycloalkyl group or a phenyl group which may be substituted, an alkoxyl group, a dialkylamino group, a halogen atom, a phenyl group, a benzyl group, a naphthyl group or a halogenated alkyl group; $R^6$ and $R^7$, and $R^8$ and $R^9$ each may be combined to form a fused ring, a trimethylene group, a tetramethylene group or a methylenedioxy group; p, q, r and s are each an integer of from 0 to 5; and p+q, and r+s are each in the range of from 0 to 5.

In the present invention, an alkyl group means a linear or branched alkyl group of from 1 to 30 carbon atoms, or more preferably, the one of from 1 to 10 carbon atoms. Specific examples of such an alkyl group are methyl, ethyl, n-propyl, isopropyl, n-butyl, isobutyl, sec-butyl, tert-butyl, n-pentyl, isopentyl, neopentyl, tert-pentyl, n-hexyl, isohexyl, 2-ethylhexyl, n-heptyl, n-octyl, n-nonyl and n-decyl. These groups may be substituted with cycloalkyl group(s) to be mentioned below.

In the present invention, a cycloalkyl group means a cycloalkyl group of from 5 to 8 carbon atoms. Specific examples of such a cycloalkyl group include cyclopentyl, cyclohexyl, cycloheptyl and cyclooctyl. These cycloalkyl groups may be substituted with the alkyl groups mentioned above.

In the present invention, an alkoxy group means a linear or branched alkoxy group of from 1 to 30 carbon atoms, or more preferably the one of from 1 to 10 carbon atoms. Specific examples of such an alkoxy group include methoxy, ethoxy, n-propoxy, isopropoxy, n-butoxy, isobutoxy, sec-butoxy, tert-butoxy, n-pentyloxy, isopentyloxy, neopentyloxy, n-hexyloxy, isohexyloxy, 2-ethylhexyloxy, n-heptyloxy, n-octyloxy, n-nonyloxy and n-decyloxy.

In the present invention, an alkyl group of a dialkylamino group means an alkyl group mentioned above, and the two alkyl groups may be the same or different. Examples of such a dialkylamino group include dimethylamino, diethylamino, di(n-propyl)amino, diisopropylamino, di(n-butyl)amino, di(n-pentyl)amino and di(n-hexyl)amino.

In the present invention, halogen atoms include a fluorine atom, a chlorine atom, a bromine atom, and an iodine atom.

In the present invention, a halogenated alkyl group means a group formed by replacing one of the hydrogen atoms of the alkyl groups mentioned above with a halogen atom mentioned above, the preferable halogen atom being a fluorine atom. Specific examples of such halogenated alkyl groups include perfluoroalkyl groups such as trifluoromethyl, pentafluoroethyl, heptafluoropropyl, etc. and fluoroalkyl such as difluoromethyl and monofluoromethyl etc.

In the present invention, a phenyl group which may be substituted means a phenyl group in which at least one of the hydrogen atoms on the said phenyl group is substituted with substituent(s) or an unsubstituted phenyl group. Examples of said substituent include an alkyl group, a cycloalkyl group, an alkoxyl group, a dialkylamino group, a halogen atom, a phenyl group, a benzyl group, a naphthyl group and a halogenated alkyl group, all of which are mentioned above.

The following is the description of the phosphine compounds of the present invention.

In the phosphine compounds of formula (1) of the present invention, $R^1$ is a hydrogen atom, an alkyl group, a cycloalkyl group or a phenyl group which may be substituted, and specific examples of such alkyl groups, cycloalkyl groups, and phenyl groups which may be substituted include those mentioned above;

$R^2$ and $R^3$ are each, the same or different, an alkyl group, a cycloalkyl group or a phenyl group which may be substituted, and specific examples of such alkyl groups, cycloalkyl groups, and phenyl groups which may be substituted include those mentioned above;

$R^4$ and $R^5$ are each, the same or different, a hydrogen atom, an alkyl group, a cycloalkyl group or a phenyl group which may be substituted, and specific examples of such alkyl groups, cycloalkyl groups, and phenyl groups which may be substituted include those mentioned above.

$R^6$, $R^7$, $R^8$ and $R^9$ are each, the same or different, a hydrogen atom, an alkyl group, a cycloalkyl group or a phenyl group which may be substituted, an alkoxyl group, a dialkylamino group, a halogen atom, benzyl group, naphthyl group, and a halogenated alkyl group, and specific examples of such alkyl groups, cycloalkyl groups, phenyl groups which may be substituted, alkoxyl groups, dialkylamino groups, halogen atoms and halogenated alkyl groups include those mentioned above.

$R^6$ and $R^7$, $R^8$ and $R^9$ each may be combined together to form a fused ring, a trimethylene group, a tetramethylene group and a methylenedioxy group. Examples of said fused ring include a naphthalene ring, an anthracene ring, a phenanthrene ring, a benzofuran ring, a benzothiophene ring, an indole ring and a quinoline ring, which are formed by condensation of $R^6$, $R^7$, $R^8$ and $R^9$ with the phenyl group on which they are present.

The phosphine compounds of formula (1) of the present invention can specifically be manufactured, for example, by the method shown below, but the present invention is not restricted by this method:

these diarylmonohalogenocyclopropane compounds (C) with lithium metal, alkyllithium or magnesium metal to give cyclopropyllithium derivatives or cyclopropylmagnesium halide derivatives, which are then reacted with various chlorophosphine derivatives.

The following is the more detailed description of the manufacturing methods of the phosphine compounds and the intermediate monohalogenocyclopropane compounds of the present invention.

In the process for manufacturing the phosphine compounds of the present invention mentioned above, diaryldihalogenocyclopropanes (B) can be obtained by reacting diarylethylenes (A) with haloforms in the presence of bases.

The amount used of the haloform is preferably from about 0.1 to 10 times or especially preferably from about 0.5 to 4 times that of diarylethylene (A) in moles.

Specific examples of the reaction solvent include hydrocarbons such as pentane, hexane, heptane, etc.; aromatic hydrocarbons such as benzene, toluene, xylene, etc.; and ethers such as diethyl ether, tetrahydrofuran, dioxane, etc. Among them, hydrocarbons such as pentane, hexane, heptane, etc. are preferably used. The amount of the solvent

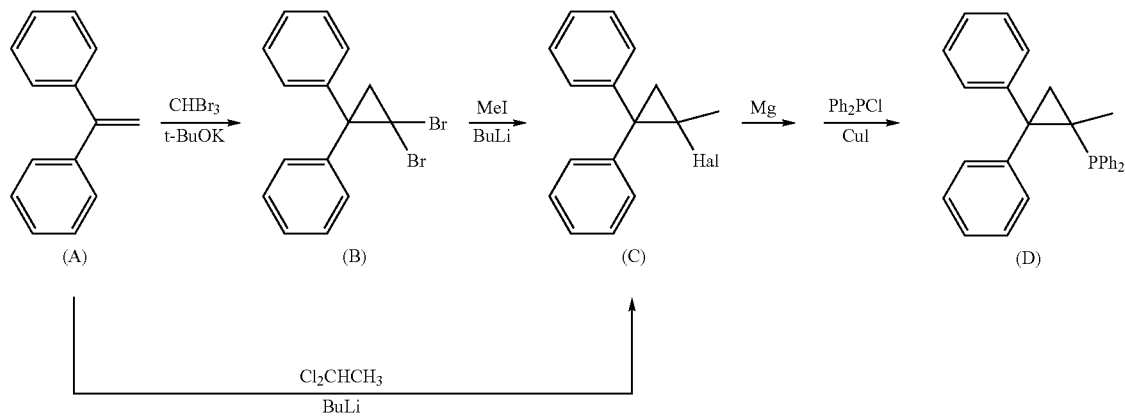

wherein Hal is chlorine or bromine, and Ph is phenyl.

One of the phosphine compounds of the present invention, 2,2-diphenyl-1-(diphenylphosphino)-1-methylcyclopropane, can be manufactured by reacting monobromocyclopropane compound (C) or monochlorocyclopropane compound (C) with magnesium metal to give a cyclopropylmagnesium halide and then by reacting the latter compound with diphenylphosphine chloride in the presence of copper iodide. The monobromocyclopropane compound (C) can, in turn, be prepared by allowing dibromocyclopropane compound (B), obtainable by the reaction of 1,1-diphenylethylene (A) with potassium tert-butoxide and bromoform, to react with n-butyllithium and methyl iodide. Alternatively, 1,1-diphenylethylene is reacted with 1,1-dichloroethane and n-butyllithium to give the monochlorocyclopropane compound (C).

Diarylmonohalogenocyclopropane compounds (C), the intermediates to the phosphine compounds of the present invention in the process shown above, are useful intermediates for the preparation of the phosphine compounds of the present invention. Namely, the phosphine compounds of the present invention are conveniently manufactured by reacting used is from about 0.2 to 30 times, or especially preferably from about 0.5 to 10 times that of the diarylethylene (A) in volume.

The reaction is usually carried out in an atmosphere of inert gases such as nitrogen, argon, etc. The reaction time is usually from 10 minutes to about 30 hours, or more preferably from 30 minutes to about 16 hours. The reaction is usually complete at the temperatures of from −80 to about 100° C., or more preferably from −20 to about 60° C., although these reaction conditions may be altered appropriately depending on the kind and amounts of the diarylethylene (A) and haloform used.

After completion of the reaction, the reaction mixture is worked-up as usual giving the objective compound.

In the process shown above, the diarylmonohalogenocyclopropanes (C) can be obtained by reacting diaryldihalogenocyclopropanes (B) with halides or dialkyl sulfate in the presence of an organometallic compound such as an organolithium compound.

Specific examples of the organolithium compound include methyllithium, ethyllithium, n-propyllithium, n-butyllithium, sec-butyllithium, tert-butyllithium and phenyllithium. Among them, n-butyllithium, sec-butyllithium, and tert-butyllithium are more preferably used. The amount of the organolithium compound used is preferably from about 0.4 to 3.0 times, and especially preferably from about 0.8 to 1.5 times that of the diaryldihalogenocyclopropane (B) used in moles.

Specific examples of the reaction solvent include ethers such as diethylether, tetrahydrofuran, dioxane, diisopropylether, dimethoxyethane, etc., among which diethylether and tetrahydrofuran are more preferably used. The amount of the solvent used is preferably from about 1.0 to 50 times, or especially preferably from about 2.0 to 25 times that of the diarylethylene (A) used in volume.

The reaction is usually carried out in an atmosphere of inert gases such as nitrogen, argon, etc. and the reaction time is usually from 10 minutes to about 40 hours, or more preferably from 30 minutes to about 18 hours, and the reaction temperature is usually from −120 to about 100° C., or more preferably from −80 to about 60° C., although these reaction conditions may be altered appropriately depending on the kind and amount of the diaryldihalogenocyclopropanes (B) and halogenides used.

After completion of the reaction, the reaction mixture is worked-up as usual giving the objective compound.

Furthermore, in the process shown above, the diarylmonohalogenocyclopropanes (C) can be obtained by reacting diarylethylenes (A) with dihalogenides (for example, 1,1-dichloroethane and 1,1-dibromoethane.) in the presence of an organometallic compound such as an organolithium compound, etc.

Specific examples of the organolithium compounds include methyllithium, ethyllithium, n-propyllithium, n-butyllithium, sec-butyllithium, tert-butyllithium and phenyllithium. Among them, n-butyllithium, sec-butyllithium and tert-butyllithium are more preferably used. And, the amount of the organolithium compound used is preferably from about 0.4 to 20 times and especially preferably from about 0.8 to 10 times that of the diarylethylene compound (A) used in moles.

Specific examples of the reaction solvent include ethers such as diethyl ether, tetrahydrofuran, dioxane, diisopropyl ether and dimethoxyethane, among which diethyl ether and tetrahydrofuran are more preferably used. The amount of the solvent used is preferably from about 1.0 to 50 times and especially preferably from about 2.0 to 25 times that of the diarylethylene (A) used in volume.

The reaction is usually carried out in an atmosphere of inert gases such as nitrogen, argon, etc., and the reaction time is usually from 10 minutes to about 40 hours, or more preferably from 30 minutes to about 18 hours, and the reaction temperature is usually from −120 to about 120° C., or more preferably at from −80 to about 60° C., although these reaction conditions may be altered appropriately depending on the kind and amount of the diaryldihalogenocyclopropanes (B) and dihalogenides used.

After completion of the reaction, the reaction mixture is worked-up as usual to give the objective compound.

The phosphine compounds (D) of the present invention are obtained, according to the procedure shown above, by reacting diarylmonohalogenocyclopropanes (C) with metal such as lithium and magnesium to give cyclopropyllithium compounds and cyclopropylmagnesium halides, respectively, followed by the reacting of those organometallic compounds with chlorophosphines.

Specific examples of the metal which can be used include lithium and magnesium. In cases where lithium is used, the amount of lithium used is preferably from about 1.0 to 3.0 times or especially preferably from about 1.5 to 2.5 times that of the substrate, diarylmonohalogenocyclopropanes (C), used in moles.

And, in cases where magnesium is used, the amount of magnesium used is preferably from about 1.0 to 3.0 times or especially preferably from about 1.2 to 1.5 times that of the substrate, diarylmonohalogenocyclopropanes (C), used in moles.

Specific examples of the reaction solvent include ethers such as diethyl ether, tetrahydrofuran, dioxane, diisopropyl ether and dimethoxyethane, among which diethyl ether and tetrahydrofuran are more preferably used. The amount of the solvent used is preferably from about 1.0 to 50 times and especially preferably from about 2.0 to 25 times that of the diarylmonohalogenocyclopropanes (C) used in volume.

The reaction is usually carried out in an atmosphere of inert gases such as nitrogen, argon, etc. The reaction time is usually from 10 minutes to about 40 hours, or more preferably from 30 minutes to about 18 hours, and the reaction temperature is usually from −120 to about 120° C., or more preferably from −80 to about 80° C., although these reaction conditions may be altered appropriately depending on the kind and amount used of the diarylmonohalogenocyclopropanes (C) and chlorophosphines.

After completion of the reaction, the reaction mixture is worked-up as usual giving the objective compound.

The phosphine compounds of formula (1) of the present invention thus obtained form, as ligands, palladium-phosphine complexes with palladium compounds.

The palladum-phosphine complexes obtainable by reacting the phosphine compounds of formula (1) of the present invention with palladium compounds can be prepared by reacting the phosphine compounds of the present invention with π-allylpalladium chloride dimer(II) or with tris(dibenzylidene)dipalladium(0) according to the methods described in the literature: for example, Y. Uozumi and T. Hayashi, J. Am. Chem. Soc., (1991), vol. 113, 9887; Gregory C. Fu, et al., J. Am. Chem. Soc., (2001), vol. 123, 2719.

Specific examples of the palladium compounds which can be used include palladium(IV) compounds such as sodium hexachloropalladate(IV) tetrahydrate, potassium hexachloropalladate(IV), etc., palladium(II) compounds such as palladium chloride(II), palladium bromide(II), palladium acetate(II), palladium(II) acetylacetonate, dichlorobis(benzonitrile)palladium(II), dichlorobis(acetonitrile)palladium (II), dichlorotetraamminepalladium(II), dichloro(cycloocta-1,5-diene)palladium(II), palladium trifluoroacetate(II) and π-allylpalladium chloride dimer, etc., and palladium(0) compounds such as tris(dibenzylideneacetone)dipalladium (0), tris(dibenzylideneacetone)dipalladium-chloroform adduct(0), etc. Among them, dichlorobis(benzonitrile)palladium(II), π-allylpailadium chloride dimer(II), tris(dibenzylideneacetone)dipalladium(0) and tris(dibenzylideneacetone)dipalladium-chloroform adduct(0) are more preferably used. The amount of the palladium compound used is preferably from about 0.1 to 8.0 times, and especially preferably from about 0.2 to 4.0 times that of the phosphine compound used in moles.

The reaction solvent is not limited to a special one, but any solvent can be used unless it does not inhibit the reaction severely. Examples of such solvents include aliphatic organic solvents such as pentane, hexane, heptane, octane, etc.; alicyclic organic solvents such as cyclohexane, methylcyclohexane, etc.; aromatic organic solvents such as benzene, toluene, xylene, etc.; ethers such as diethyl ether, diisopropyl ether, dimethoxyethane, tetrahydrofuran, dioxane, dioxolane, etc.; acetonitrile; dimethylformamide; dimethyl sulfoxide; and hexamethylphosphoric triamide.

Among them, aromatic organic solvents such as benzene, toluene, xylene, etc., and ethers such as diethyl ether, dimethoxyethane, tetrahydrofuran, dioxane, etc. are more preferably used. The amount of the solvent used is preferably from about 1.0 to 50 times, and especially preferably from about 2.0 to 25 times that of the phosphine compound used in volume.

The reaction is usually carried out in an atmosphere of inert gases such as nitrogen, argon, etc. The reaction time is usually from 10 minutes to about 40 hours, or more preferably from 30 minutes to about 18 hours, and the reaction temperature is usually from −20 to about 160° C., or more preferably from 0 to about 120° C., although these reaction conditions may be altered appropriately depending on the kind and amount of the phosphine compounds used and the palladium compounds used.

After completion of the reaction, the reaction mixture is worked-up as usual giving the objective compound.

The palladium-phosphine complexes obtainable by the reaction of the phosphine compounds of the present invention with palladium compounds can be used as catalysts in carbon to carbon bond-forming reactions in compounds having unsaturated bonds (for example, Suzuki coupling reaction, Stille coupling reaction, Negishi coupling reaction, Sonogashira coupling reaction, α-arylation of carbonyl compounds, alkoxycarbonylation, etc.), carbon to nitrogen bond-forming reactions (for example, arylamination reaction, vinylamination reaction, etc.), and carbon to oxygen bond-forming reactions (for example aryletherification reaction, vinyletherification reaction, etc.).

According to the present invention, an unsaturated compound or an aromatic compound can be produced advantageously by the use of the palladium-phosphine complex or alternatively by the use of the phosphine compound and the palladium compound.

One of the manufacturing methods of the present invention is selected from the reactions below:

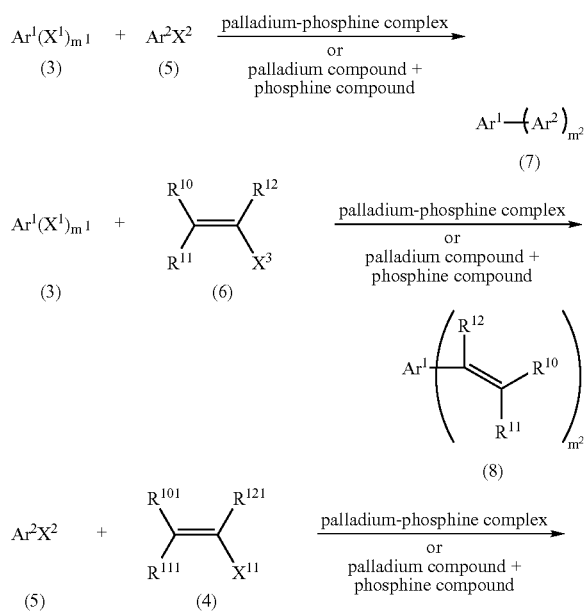

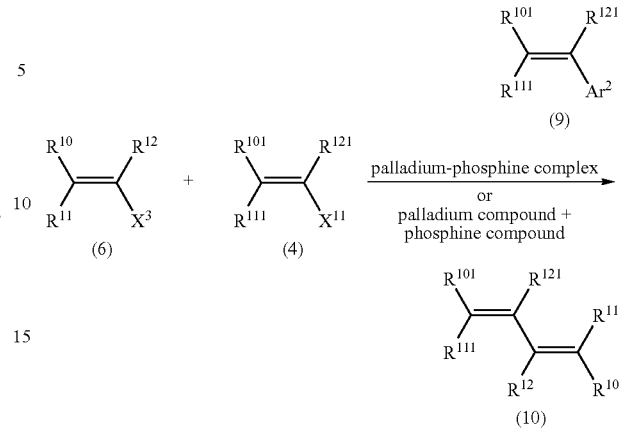

(Hetero)aryl compounds of formula (3) which can be used in the present invention include (hetero)aryl bromides, (hetero)aryl chlorides, (hetero)aryl iodides, (hetero)aryltrifluoromethane sulfonates, (hetero)arylmethane sulfonates, (hetero)aryl para-toluenesulfonates and (hetero)aryl compounds having 1-4 halogen atoms or sulfonate moieties.

Specific examples of the (hetero)aryl compounds include aryl bromides such as bromobenzene, 1,4-dibromobenzene, 1,3,5-tribromobenzene, p-bromoanisole, p-bromotoluene, o-bromophenol, p-bromophenol, 2-bromobenzotrifluoride, 4-bromobenzotrifluoride, mesityl bromide, 4-bromophenethyl alcohol, 2-bromo-m-xylene, 2-bromo-p-xylene, 5-bromo-m-xylene, 1-bromo-4-(trifluoromethoxy)benzene, 2-bromobiphenyl, 4-bromobiphenyl, 4-bromo-1,2-(methylenedioxy)benzene, 1-bromonaphthalene, 2-bromonaphthalene, 1-bromo-2-methylnaphthalene, 1-bromo-4-methylnaphthalene, 1,4-dibromonaphthalene, 4,4'-dibromobiphenyl, 2-bromothiophene, 2-bromopyridine, 9-bromophenanthrene, 2-bromofuran, 2,4-difluorobromobenzene, 2,4-di(trifluoromethyl)bromobenzene, 4-bromodimethylaminobenzene, 4-bromobenzonitrile, tetrabromoperylene, dibromoanthanthrone, etc.; and those compounds which are formed by replacing the bromine atom(s) in the aryl bromides mentioned above with chlorine or iodine atom(s).

Examples of the sulfonates include those compounds which are formed by replacing the bromine atom in the bromide mentioned above with either a trifluoromethanesulfonyloxy group, a methanesulfonyloxy group or a para-toluenesulfonyloxy group. These sulfonates can be readily obtained by treating the precursor phenols with sulfonylating agents such as, for example, trifluoromethanesulfonic anhydride, methanesulfonyl chloride, etc. in the presence of bases such as triethylamine, etc.

Unsaturated compounds represented by formula (4) in the present invention include those compounds having a double bond formed between a carbon atom carrying a substituent $X^{11}$ which serves as the leaving group in the reaction, and a carbon atom adjacent to it, such as, for example, vinyl halogenides, vinyl sulfonates and their analogs. Typical examples of the bromides as such vinyl halogenides and their analogs include bromoethylene, 1-bromopropene, 2-bromopropene, 2-bromo-2-butene, 1-bromo-1-butene, 1-bromo-2-butene, bromocyclopentene, bromocyclohexene, α-bromostylene, β-bromostylene, 2,2-diphenyl-1-bromoethylene, 1,2-diphenylbromoethylene, 3-bromo-2-propen-1-ol, 2-bromo-2-propen-1-ol, methyl 2-bromoacrylate and 2-bromoacrylonitrile.

Examples of the sulfonates and their analogs include, taking trifluoromethanesulfonates as representatives, trifluoromethanesulfonyloxyethylene, 1-trifluoromethanesulfonyloxypropene, 2-trifluoromethanesulfonyloxypropene, trifluoromethanesulfonyloxycyclopentene, trifluoromethanesulfonyloxycyclohexene and 1-trifluoromethanesulfonyloxy-1-methoxyethylene.

(Hetero)aryl compounds of formula (5), which can be used in the present invention, include boronic acids, boronic esters, trialkylaryltin compounds, arylmagnesium halides, arylzinc halides, dialkylarylaluminium compounds and aryllithium compounds.

Although there is no particular limitation for the boronic acids, examples of the boronic acids include boronic acids such as phenylboronic acid, 4-methylphenylboronic acid, 2-thienylboronic acid, 2-furylboronic acid, 2-pyridylboronic acid, 2,3,4,5,6-pentafluorophenylboronic acid, 2-fluorophenylboronic acid, 4-chlorophenylboronic acid, 2-bromophenylboronic acid, 4-iodophenylboronic acid, 2,4-difluorophenylboronic acid, 4-trifluoromethylphenylboronic acid, 3-cyanophenylboronic acid, 4-formylphenylboronic acid, 4-methoxyphenylboronic acid, 1-naphthylboronic acid, ferrocenylboronic acid, 4-hydroxyphenylboronic acid, etc., and esters (for example, dimethyl ester, diethyl ester, dipropyl ester and pinacol ester, etc.) of those arylboronic acids mentioned above.

Although there is no particular limitation for the trialkyltin compounds, examples of the trialkyltin compounds include phenyltrimethyltin, phenyltriethyltin, phenyltributyltin, 2-methylphenyltributyltin, 2,4,6-trimethylphenyltributyltin, 4-methoxyphenyltributyltin, 2-pyridyltributyltin, 3-pyridyltributyltin, 2-thienyltributyltin, 3-thienyltributyltin and 2-furyltributyltin.

Although there is no particular limitation for the arylmagnesium halides, arylzinc halides, dialkylarylaluminum compounds and aryllithium compounds, examples of said compounds are those such as phenylmagnesium halide, 4-biphenylmagnesium halide, 2-biphenylmagnesium halide, 4-methoxyphenylmagnesium halide, 4-methylphenylmagnesium halide, 3-methoxyphenylmagnesium halide, 3-methylphenylmagnesium halide, 2-methoxyphenylmagnesium halide, 2-methylphenylmagnesium halide, 2-pyridylmagnesium halide, 2-thienylmagnesium halide, 2-furylmagnesium halide, phenylzinc halide, 4-biphenylzinc halide, 2-biphenylzinc halide, 2-methylphenylzinc halide, 3-methylphenylzinc halide, 4-methylphenylzinc halide, 2,6-dimethylphenylzinc halide, 2,4,6-trimethylphenylzinc halides, 4-methoxyphenylzinc halides, 2-pyridylzinc halides, 3-pyridylzinc halides, 2-thienylzinc halides, 2-furylzinc halides, phenyldimethylaluminum, phenyldiethylaluminum, phenyldipropylaluminum, phenyldiisopropylaluminum, phenyldibutylaluminum, phenyldiisobutylaluminum, 2-methylphenyldiethylalluminum, 4-methoxyphenyldiethylaluminum, 2-thienyldiethylaluminum, phenyllithium, 2-methylphenyllithium, 4-methoxyphenyllithium, 2-thienyllithium, 2-pyridyllithium, 2-furyllithium, etc.

Unsaturated compounds of formula (6) include olefins which may be substituted, terminal acetylene compounds which may be substituted, acrylic acid esters and acrylonitriles which may be substituted on the α- or β-position, (hetero)aryl compounds which have a vinyl group and may have additional substituent (s), alkenyl boronic acids, alkenyl boronic acid esters, trialkylalkenyltin compounds, alkenylmagnesium halides, alkenylzinc halides, dialkylalkenylaluminum compounds and aklenyllithium compounds.

Specific examples of the olefins which may be substituted include ethylene, propene, 1-butene, 2-butene, 1-heptene, 2-heptene, cyclopentene, cyclohexene, methylcyclohexene, allyl alcohol, methacryl alcohol, homoallyl alcohol, crotyl alcohol, crotonaldehyde, vinyl butyl ether and allylbenzene.

Although there is no particular limitation for the acrylic acid esters and acrylonitriles which may be substituted on the α- or β-position, examples of such groups include methyl acrylate, ethyl acrylate, butyl acrylate, tert-butyl acrylate, ethyl methacrylate, ethyl crotonate, acrylonitrile, methacrylonitrile and crotononitrile.

Although there is no particular limitation for the (hetero) aryl compounds which have a vinyl group and may have additional substituent(s), examples as such group include styrene, stilbene, 4-methylstyrene, 3-methylstyrene, 4-vinylmethoxybenzene, β-methoxystyrene, α-methylstyrene, 2-vinylthiophene, 3-vinylthiophene, 2-vinylpyridine and 2-vinylfuran.

Although there is no particular limitation for the alkenylboronic acids, examples of such group include bononic acids such as vinylboronic acid, 1-propen-1-ylboronic acid, 1-propen-2-ylboronic acid, 1-buten-1-ylboronic acid, 1-buten-2-ylboronic acid, 2-buten-2-ylboronic acid, 1-penten-1-ylboronic acid, α-styrylboronic acid, β-styrylboronic acid, 1,2-diphenylethenylboronic acid, 2,2-diphenylethenylboronic acid, cyclopentenylboronic acid, cyclohexenylboronic acid, 2-methylcyclohexenylboronic acid, etc. and their esters (for example, dimethyl esters, diethyl esters, dipropyl esters, pinacol esters, etc.) of those alkenylboronic acids.

Although there is no particular limitation for the trialkylalkenyltin compounds, examples of such compounds include vinyltrimethyltin, vinyltriethyltin, vinyltripropyltin, vinyltributyltin, 1-propen-1-yltributyltin, 1-buten-1-yltributyltin, 1-ethoxyethenyltributyltin, α-styryltributyltin, β-styryltributyltin, 1,2-diphenylethenyltributyltin, 2,2-diphenylethenyltributyltin, cyclopentenyltributyltin, cyclohexenyltributyltin.

Although there is no particular limitation for the alkenylmagnesium halides, alkenylzinc halides, dialkylalkenylaluminum compounds and alkenyllithium compounds, examples of such groups include compounds such as vinylmagnesium halides, 1-propen-1-ylmagnesium halides, 1-propen-2-ylmagnesium halides, 1-buten-1-ylmagnesium halides, α-styrylmagnesiumhalides, β-styrylmagnesium halides, 1,2-diphenylethenylmagnesium halides, 2,2-diphenylethenylmagnesiumhalides, cyclopentenylmagnesium halides, cyclohexenylmagnesium halides, vinylzinc halides, 1-propen-1-ylzinc halides, 1-propen-2-ylzinc halides, 1-buten-1-ylzinc halides, α-stylylzinc halides, β-stylylzinc halides, 1,2-diphenylethenylmagnesium halides, 2,2-diphenylethenylmagnesium halides, cyclopentenylzinc halides, cyclohexenylzinc halides, vinyldimethylaluminum, vinyldiethylaluminum, vinyldipropylaluminum, vinyldiisopropylaluminum, vinyldibutylaluminum, vinyldiisobutylaluminum, 1-propen-1-yldiethylaluminum, β-styryldiethylaluminum, vinyllithium, 1-propen-1-yllithium, β-styryllithium, cyclopentenyllithium, cyclohexenyllithium, etc.

Although there is no particular limitation for the terminal acetylene compounds which may be substituted, examples of such compounds include acetylene, propyne, 1-butyne, 1-pentyne, 1-hexyne, 1-heptyne, 1-octyne, phenylacetylene, 2-propyn-1-ol, 3-butyn-1-ol, 2-methyl-3-butyn-2-ol, 1-ethynylcyclohexanol and trimethylsilylacetylene.

In this manufacturing method, it is only required that not less than 1 mole of the boronic acids, trialkylaryltin compounds, arylmagnesium halides, arylzinc halides, dialkylarylaluminum compounds and aryllithium compounds exist in the reaction system per 1 mole of the aromatic compound (3) or the unsaturated compound (4). It is more preferable, however, that those compounds exist in the reaction system in an amount of 1 to 10 times that of the aromatic compound (3) or the unsaturated compound (4) in moles, because recovery of the unchanged material: boronic acids, trialkylaryltin compounds, arylmagnesium halides, arylzinc halides, dialkylarylaluminum compounds and aryllithium compounds, becomes complicated.

In this manufacturing method, it is only required that not less than 1 mole of the terminal acetylene compounds which may be substituted, the acrylic esters which may be substituted on the α- or β-position and the (hetero)aryl compounds and acrylonitriles which have a vinyl group and may have additional substituent(s) exist in the reaction system per 1 mole of the aromatic compound (3) or the unsaturated compound (4). It is more preferable, however, that those compounds exist in the reaction system in an amount of 1 to 10 times that of the aromatic compound (3) or the unsaturated compound (4) in moles, because recovery of the unchanged material including terminal acetylene compounds which may be substituted, acrylic esters which may be substituted on the α- or β-position, and (hetero)aryl compounds and acrylonitriles which have a vinyl group and may have additional substituent(s), becomes complicated.

In this manufacturing method, it is appropriate to use bases as auxiliary agents. The bases to be used can be selected from inorganic and/or organic bases without being specifically restricted to those cited. Examples of such bases are carbonates of alkali metals or alkaline earth metals such as lithium carbonate, sodium carbonate, potassium carbonate, rubidium carbonate, cesium carbonate, magnesium carbonate, calcium carbonate, barium carbonate, etc.; alkali metal alkoxides such as sodium methoxide, sodium ethoxide, sodium phenoxide, sodium tert-butoxide, potassium methoxide, potassium ethoxide, potassium phenoxide, potassium tert-butoxide, lithium methoxide, lithium ethoxide, lithium phenoxide, lithium tert-butoxide, etc.; hydroxides of alkali metals or alkaline earth metals such as sodium hydroxide, potassium hydroxide, lithium hydroxide, barium hydroxide, etc.; phosphates of alkali metals such as lithium phosphate, potassium phosphate, sodium phosphate, etc.; amines such as trimethylamine, triethylamine, triisopropylamine, tricyclohexylamine, diethylamine, diisopropylamine, methylmorpholine, pyridine and picoline; and alkali metal fluorides such as lithium fluoride, potassium fluoride, sodium fluoride, cesium fluoride, rubidium fluoride, etc.

The amount of the base used is preferably not less than 1 mole per 1 mole of the aromatic compound (3) or the unsaturated compound (4). With less than 1 mole equivalent of the base, the yield of the unsaturated compound obtained by the method of the present invention may be reduced. Although addition of even a large excess amount of the base hardly affects adversely on the yield of the unsaturated compound obtained, but it complicates the work-up procedure after completion of the reaction. Thus, the amount of the base used is more preferably in the range of from 1 to 5 times in moles.

The methods mentioned above for manufacturing unsaturated compounds are usually carried out in the presence of a solvent inert to the reactions. The solvents which can be used are not restricted to any specific ones so long as they do not inhibit the reactions extremely, but include aliphatic organic solvents such as pentane, hexane, heptane, octane, etc.; alicyclic organic solvents such as cyclohexane, methylcyclohexane, etc.; aromatic organic solvents such as benzene, toluene, xylene, etc.; ethers such as diethyl ether, diisopropyl ether, dimethoxyethane, tetrahydrofuran, dioxane, dioxolane, etc.; acetonitrile; dimethylformamide; dimethylsulfoxide; hexamethylphosphotriamide, etc. Among these solvents, aromatic organic solvents such as benzene, toluene, xylene, etc., and ethers such as diethyl ether, dimethoxyethane, tetrahydrofuran, dioxane, etc. are used more preferably.

The present invention can be carried out in an atmosphere of inert gases such as nitrogen, argon, etc., under normal pressure or under increased pressure.

The present invention can be carried out at temperatures in the range from about 0° C. to 300° C., or more preferably at temperatures in the range from about 20° C. to 200° C.

The reaction time of the present invention varies depending on the kind of the reaction and the reaction temperature, but can be selected from a range from about several minutes to 72 hours.

After completion of the reaction, the reaction mixture is treated by the ordinary methods to give the objective compound.

A further manufacturing method of the present invention is the one selected from the reactions below:

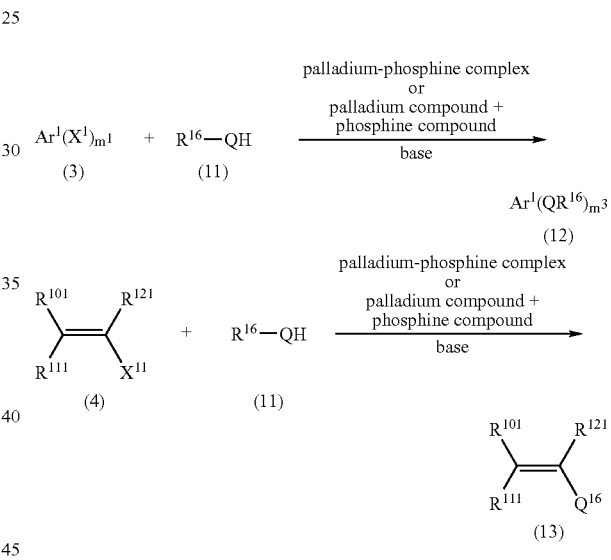

Thus, an aromatic compound (3) or an unsaturated compound (4) is reacted with an oxygen or a nitrogen compound (11) in the presence of a base by using the palladium-phosphine complex of the present invention or by using pallasium compound and phosphine compound of the present invention as catalyst to give a compound (12): an aromatic ether or an aromatic nitrogen compound, and a compound (13): an alkenyl ether or alkenyl nitrogen compound.

Examples of the (hetero)aryl compound represented by formula (3) and the unsaturated compounds represented by formula (4) used in the present invention, include the same ones as those mentioned above.

Examples of the oxygen compound of formula (11) used in the present invention include alcohols which may be substituted, phenols which may be substituted and heterocyclic compounds which have hydroxyl group(s) and may further be substituted, and examples of the nitrogen compound of formula (11) used in the present invention include primary amines, secondary amines, amides, imines, (di) alkylamines which may be substituted, (di)arylalkylamines which may be substituted, (di)heteroarylamines which may be substituted, alkylarylamines which may be substituted, alkylheteroarylamines which may be substituted, and amides and imines which may be substituted.

Specific examples of the oxygen compound include the followings: namely, phenol, 2-methoxyphenol, 2-tert-butylphenol, 2-methylphenol, 2-dimethylaminophenol, 3-methoxyphenol, 3-tert-butylphenol, 3-methylphenol, 3-dimethylaminophenol, 4-methoxyphenol, 4-tert-butylphenol, 4-methylphenol, 4-dimethylaminophenol, 1-naphthol, 2-biphenol, methanol, ethanol, 1-propanol, 2-propanol, 1-butanol, 2-butanol, and tert-butanol, although they are not restricted to those cited.

Although specific examples of the nitrogen compounds are shown below, they are not limited thereto. As primary amines, there are exemplified by aliphatic primary amines such as ethylamine, propylamine, butylamine, isobutylamine, tert-butylamine, pentylamine, cyclopentylamine, hexylamine, cyclohexylamine, heptylamine, octylamine, etc., and aromatic primary amines such as aniline, m-fluoroaniline, p-fluoroanline, o-anisidine, m-anisidine, o-toluidine, m-toluidine, p-toluidine, 2-naphthylamine, 2-aminobiphenyl, 4-aminobiphenyl, 3,4-methylenedioxyaniline, m-xylidine, p-xylidine, m-phenylenediamine, etc.

Although there is no particular limitation for the secondary amines, they include, for example, cyclic secondary amines such as piperazine, 2-methylpiperazine, homopiperazine, N-methylhomopiperazine, 2,6-dmethylpiperazine, N-methylpiperazine, N-ethylpiperazine, N-ethoxycarbonylpiperazine, N-benzylpiperazine, morpholine, 2,6-dilmethylmorpholine, piperidine, 2,6-dimethylpiperidine, 3,3-dimethylpiperidine, 3,5-dimethylpiperidine, 2-ethylpiperidine, 4-piperidone, pyrrolidine, 2,5-dimethylpyrrolidine, carbazole, indole, indoline, acridone, quinacridone, etc., and acyclic secondary amines such as dimethylamine, diethylamine, and N-methylaniline, N-ethylanilne, N-methylbenzylamine, N-methylphenethylamine and diphenylamine derivatives which may be further substituted on the aromatic ring.

Although there is no particular limitation for the imines, they include, for example, benzophenone imine, 4,4'-dimethoxybenzophenone imine, etc.;

Although there is no particular limitation for the amides, they include, for example, 2-azetidinone (β-propiolactam), γ-butyrolactam, δ-valerolactam, ε-caprolactam, acetamide, propionamide, cyclohexylcarboxamide, benzamide, N-methylformamide, N-methylacetamide, N-ethylacetamide, N-methylcyclohexylcarboxamide, N-methylbenzamide, etc.

In this manufacturing method, the oxygen or nitrogen compound (11) is to be present in the reaction system in the range of not less than 1 mole per 1 mole of the aromatic compound (3) or the unsaturated compound (4). It is more preferable, however, for the oxygen or nitrogen compound to exist in the reaction system in the range of 1 to 2 moles per 1 mole of the aromatic compound (3) or the unsaturated compound (4), because recovery of the unreacted oxygen or nitrogen compound (11) which becomes complicated.

In the manufacturing method of the present invention, it is preferable to use bases as auxiliary agents. Such bases to be used can be selected from inorganic bases and/or organic bases and are not restricted to specific ones. Thus, examples of bases used preferably include carbonates of alkali metals or alkaline earth metals such as lithium carbonate, sodium carbonate, potassium carbonate, rubidium carbonate, cesium carbonate, magnesium carbonate, calcium carbonate, barium carbonate, etc.; alkoxides of alkali metals such as sodium methoxide, sodium ethoxide, sodium phenoxide, sodium tert-butoxide, potassium methoxide, potassium ethoxide, potassium phenoxide, potassium tert-butoxde, lithium methoxide, lithium ethoxide, lithium phenoxide, lithium tert-butoxide, etc.; phosphates of alkali metals such as lithium phosphate, potassiumphosphate, sodium phosphate, etc.

The amount of the base used is preferably not less than 1 mole per 1 mole of the aromatic compound (3) or the unsaturated compound (4). With less than 1 mole of the base, the yield of the unsaturated compound obtained by the method of the present invention may be reduced. Although addition of even a large excess amount of the base hardly affects the yield of the unsaturated compound obtainable by the manufacturing method of the present invention, but it complicates the work-up procedure after completion of the reaction. Thus, preferable amount of the base used is in the range of 1 to 5 times that of the aromatic compound (3) or the unsaturated compound (4) in moles.

The manufacturing method of the unsaturated compounds mentioned above is usually carried out in the presence of a solvent inert to the reaction. Although any solvent can be used without particular restriction so long as it does not inhibit the reaction severely, examples of such solvents preferably used include aliphatic organic solvents such as pentane, hexane, heptane, octane, etc.; alicyclic organic solvents such as cyclohexane, methylcyclohexane, etc.; aromatic organic solvents such as benzene, toluene, xylene, etc.; ethers such as diethyl ether, diisopropyl ether, dimethoxyethane, tetrahydrofuran, dioxane, dioxolane, etc.; acetonitrile, dimethylformamide, dimethylsulfoxide, hexamethylphosphotriamide. Among them, aromatic organic solvents such as benzene, toluene, xylene, etc., and ethers such as diethyl ether, dimethoxyethane, tetrahydrofuran, dioxane, etc. are used more preferably.

The present invention can be carried out in an atmosphere of inert gases such as nitrogen, argon, etc., under normal pressure or under increased pressure.

The present invention can be carried out at temperatures in the range from about 0° C. to 300° C., or more preferably at temperatures in the range of about 20° C. to 200° C.

The reaction time of the present invention varies depending on the kind of the reaction and the reaction temperature, but can be selected from a range of about several minutes to 72 hours.

After completion of the reaction, the reaction mixture obtained is treated by the ordinary methods to give the objective compound.

Another manufacturing method of unsaturated compounds of the present invention is the one according to the reaction below:

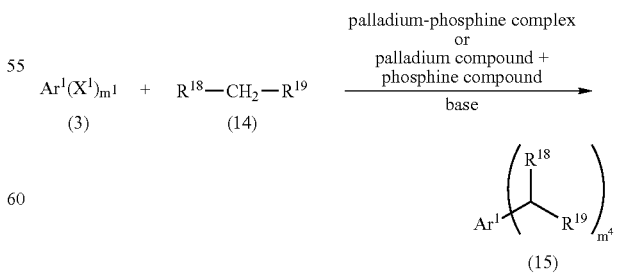

Thus, an aromatic compound (3) and a carbonyl or cyano compound (14) are reacted, in the presence of a base by using the palladium-phosphine complex or by using palladium compound and phosphine compound of the present invention as catalyst to give an aromatic carbonyl or cyano compound (15).

Examples of the (hetero)aryl compound of formula (3), which is used in the present invention, include those similar to those mentioned above.

The compounds of formula (14) which are employable in the present invention are selected from the compounds which have a methylene group are able to generate a carboanion under the influence of a base, namely so called active-methylene compounds. Examples of such compounds include monoketones, diketones, esters, diesters, nitriles and amides. Specific examples of such compounds include acetone, 2-butanone, 2-pentanone, 3-pentanone, acetophenone, 2,4-pentanedione, 2,4-hexanedione, 1,3-cyclopentanedione, 1,3-cyclohexanedione, 1,3-diphenyl-1,3-propanedione, methyl acetate, ethyl acetate, butyl acetate, tert-butyl acetate, phenyl acetate, ethyl butylate, ethyl isobutylate, ethyl 2-phenylacetate, diethyl succinate, γ-butyrolactone, dimethyl malonate, diethyl malonate, di-tert-butyl malonate, dimethyl methylmalonate, diethyl ethylmalonate, acetonitrile, propionitrile, butyronitrile, isobutyronitrile, malononitrile, methylmalononitrile, N,N-dimethylacetamide, N-methylacetamide, N,N-ethylacetamide, N,N-diphenylacetamide, propionamide, N-methylpropionamide, N,N-dimethylpropionamide, β-propiolactam and N-methyl-β-propiolactam, γ-butyrolactam, without being restricted specifically to those cited.

In this manufacturing method, it is only required that not less than 1 mole of the compound (14) exist in the reaction system relative to the figure $m^1$ of the aromatic compound (3). It is more preferable, however, for the compound (14) to exist in the reaction system in the range of 1 to 2 times moles relative to the figure $m^1$ of compound (3), because recovery of the unreacted compound (14) becomes complicated, In this manufacturing method, it is appropriate to use bases as auxiliary agents. The bases to be used can be selected from inorganic bases and/or organic bases without being restricted to specific ones. Examples of such bases include carbonates of alkali metals or alkaline earth metals such as lithium carbonate, sodium carbonate, potassium carbonate, rubidium carbonate, cesium carbonate, magnesium carbonate, calcium carbonate, barium carbonate, etc.; alkoxides of alkali metals such as sodium methoxide, sodium ethoxide, sodium phenoxide, sodium tert-butoxide, potassium methoxide, potassium ethoxide, potassium phenoxide, potassium tert-butoxide, lithium methoxide, lithium ethoxide, lithium phenoxide, lithium tert-butoxide, etc.; phosphates of alkali metals such as lithium phosphate, potassium phosphate, sodium phosphate, etc.; and amines such as trimethylamine, triethylamine, triisopropylamine, tricyclohexylamine, diethylamine, diisopropylamine, etc.

The amount of the base used is preferably not less than equimolar relative to the figure m of the aromatic compound (3) in m. With less than 1 mole equivalent of the base, the yield of the unsaturated compound obtained by the manufacturing method of the present invention may be reduced. Although addition of even a large excess amount of the base hardly affect adversely the yield of the unsaturated compound obtained by the manufacturing method of the present invention, but it complicates the work-up procedure after completion of the reaction. Thus, the amount of the base used is more preferably in the range from 1 to 5 times in moles.

The manufacturing method of unsaturated compounds mentioned above is usually carried out in the presence of a solvent inert to the reaction. Any solvent can be used without particular limitation so long as they do not inhibit the reaction severely. Examples of such solvents include aliphatic organic solvents such as pentane, hexane, heptane, octane, etc.; alicyclic organic solvents such as cyclohexane, methylcyclohexane, etc., aromatic organic solvents such as benzene, toluene, xylene, etc.; ethers such as diethyl ether, diisopropyl ether, dimethoxyethane, tetrahydrofuran, dioxane, dioxolane, etc.; acetonitrile, dimethylformamide, dimethylsulfoxide, hexamethylphosphotriamide. Among them, aromatic organic solvents such as benzene, toluene, xylene, etc., and ethers such as diethyl ether, dimethoxyethane, tetrahydrofuran, dioxane, etc. are used more preferably.

The present invention can be carried out in an atmosphere of inert gases such as nitrogen or argon under normal pressure or under increased pressure.

The present invention can be carried out at temperatures in the range from about 0° C. to 300° C., or more preferably at temperatures in the range from about 20° C. to 200° C.

The reaction time of the present invention varies depending on the kind of the reaction and the reaction temperature, but can be selected from a range of about several minutes to 72 hours.

After completion of the reaction, the reaction mixture obtained is treated by the ordinary methods to give the objective compound.

Further, one of the manufacturing methods of the unsaturated compounds of the present invention is the one according to the reaction below:

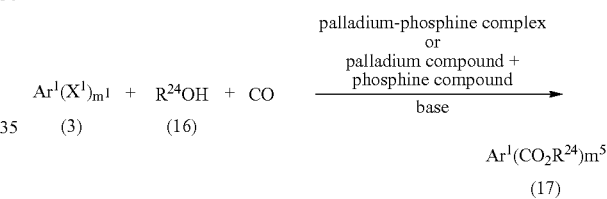

Namely, an aromatic compound (3), an alcohol (16) and carbon monoxide are reacted in the presence of a base by using the palladium-phosphine complex of the present invention or by using palladium compound and phosphine compound of the present invention as catalyst to give an aromatic carboxylic ester (17).

Examples of the aromatic compound (3) which can be used in this invention include those similar to those mentioned above. The alcohols are those of 1–4 carbon atoms, including methanol, ethanol, n-propanol, isopropanol, n-butanol, isobutanol and sec-butanol.

In this manufacturing method, the alcohol (16) is to be present in the reaction system in an amount of a range of not less than equimolar relative to the figure $m^1$ of the aromatic compound (3). However, in cases where recovery of the unreacted alcohol (16) becomes complicated, it is more preferable for the alcohol to exist in the reaction system in the range from 1 to 3 times $m^1$ of the aromatic compound (3) in moles.

In this manufacturing method, it is appropriate to use bases as auxiliary agents. The bases to be used can be selected from inorganic bases and/or organic bases without particular restriction. Examples of such bases include carbonates of alkali metals or alkaline earth metals such as lithium carbonate, sodium carbonate, potassium carbonate, rubidium carbonate, cesium carbonate, magnesium carbonate, calcium carbonate, barium carbonate, etc.; alkoxides of alkali metals such as sodium methoxide, sodium ethoxide, sodium phenoxide, sodium tert-butoxide, potassium methoxide, potassium ethoxide, potassium phenoxide, potassium tert-butoxide, lithium methoxide, lithium ethoxide, lithium phenoxide, lithium tert-butoxide, etc.; alkali metal or alkaline earth metal hydroxides such as sodium hydroxide, potassium hydroxide, lithium hydroxide, barium hydroxide, etc.; phosphates of alkali metals such as lithium phosphate, potassium phosphate, sodium phosphate, etc.; and amines such as trimethylamine, triethylamine, triisopropylamine, tricyclohexylamine, diethylamine, diisopropylamine, etc.; and acetates of alkali metals such as sodium acetate, potassium acetate, lithium acetate, etc.

The amount of the base used is preferably not less than equimolar relative to the figure $m^1$ of the aromatic compound (3). With less than 1 mole equivalent of the base, the yield of the unsaturated compound obtained by the manufacturing method of the present invention may be reduced. Although addition of even a large excess amount of the base hardly affects adversely the yield of the unsaturated compound obtained by the manufacturing method of the present invention, it complicates the work-up procedure after completion of the reaction. Thus, the amount of the base used is more preferably in the range from 1 to 5 times in moles.

The manufacturing method of unsaturated compounds mentioned above is usually carried out in the presence of a solvent inert to the reaction. Although there is no particular limitation for the solvent, any solvent can be used so long as it does not inhibit the reaction severely. Examples of such solvent include aliphatic organic solvents such as pentane, hexane, heptane, octane, etc.; alicyclic organic solvents such as cyclohexane, methylcyclohexane, etc.; aromatic organic solvents such as benzene, toluene, xylene, etc.; ethers such as diethyl ether, diisopropyl ether, dimethoxyethane, tetrahydrofuran, dioxane, dioxolane, etc.; acetonitrile, dimethylformamide, dimethylsulfoxide, hexamethylphosphotriamide. Among them, aromatic organic solvents such as benzene, toluene, xylene, etc., and ethers such as diethyl ether, dimethoxyethane, tetrahydrofuran, dioxane, etc. are used more preferably.

The present invention is usually carried out under pressure with carbon monoxide. The pressure of the carbon monoxide used is in the range from about 0.1 to 30 MPa, or more preferably in the range of about 0.1 to 20 MPa.

The reaction of the present invention can be carried out at temperatures in the range from about 0° C. to 300° C., or more preferably at temperatures in a range from about 20° C. to 200° C.

The reaction time of the present invention varies depending on the individual reaction and the reaction temperature, but can be selected from a range of about several minutes to 72 hours.

After completion of the reaction, the reaction mixture is treated by the ordinary methods to give the objective compound.

The palladium-phosphine complexes, which are used in the present invention as catalyst, can be obtained in catalytically active forms even when they are prepared by the so-called in situ method, namely by adding the palladium compound and the phosphine compound directly to the reaction system.

BEST MODE FOR CARRYING OUT THE INVENTION

The present invention will be explained in more detail with reference to the following Examples, but the invention should not be restricted thereby.

The apparatus used to measure each of the following physical properties in Examples is as follows:
1) $^1$H-NMR spectrum: a GEMINI2000 (manufactured by Varian Inc.) or a DRX-500 (manufactured by Bruker Co.); internal standard: tetramethylsilane.
2) $^{31}$P-NMR spectrum: a DRX-500 apparatus (manufactured by Bruker Co.); external standard: 85 weight % phosphoric acid.
3) Gas-chromatograph: a GC 353 (manufactured by GL Science Co.); column: a NB-1 (30 m×0.25 mm) (manufactured by GL Science Co.); internal standard: biphenyl.

EXAMPLE 1

Preparation of 2,2-diphenyl-1-(diphenylphosphino)-1-methylcyclopropane (1) Preparation of 1,1-dibromo-2,2-diphenylcyclopropane Under a nitrogen atmosphere, potassium tert-butoxide (14.8 g, 132 mmol), diphenylethylene (13.2 g, 73.3 mmol) and hexane (75 ml) were placed in a reaction flask and cooled to −5° C. To this, bromoform (24.1 ml, 95.4 mmol) was added gradually, and the mixture was stirred at the same temperature for 30 minutes. Then, water was added to the reaction mixture and the organic layer was extracted with toluene. The toluene extract was dried over anhydrous magnesium sulfate and then the solvent was removed under reduced pressure. The residue was recrystallized from a mixed solvent of isopropanol and toluene to give the title compound (14.4 g, 56%) as white crystal.

$^1$H-NMR(CDCl$_3$) δ 2.47(s, 3H), 7.16–7.37(m, 6H), 7.46–7.57(m, 4H).

(2) Preparation of 1-bromo-2,2-diphenyl-1-methylcyclopropane

Under a nitrogen atmosphere, 1,1-dibromo-2,2-diphenylcyclopropane(10.6 g, 30.0 mmol) obtained in Example 1-(1) and THF (tetrahydrofuran, 120 ml) were placed in a reaction flask and cooled to −70° C. To the mixture, n-butyllithium in hexane (20 ml, 1.57M, 31.4 mmol) was added gradually, and the mixture was stirred at the same temperature for 30 minutes. Methyl iodide (2.1 ml, 33 mmol) was added to the reaction mixture and the resulting mixture was stirred for 30 minutes and then warmed to room temperature. Then, water was added to the reaction mixture and the organic layer was extracted with toluene. The toluene extract was dried over anhydrous magnesium sulfate and then the solvent was removed under reduced pressure. The residue was recrystallized from methanol to give the title compound (7.28 g, 89%) as white crystal.

$^1$H-NMR(CDCl$_3$) δ 1.71(d, J=6.3 Hz, 1H), 1.75(s, 3H), 1.97(d, J=6.3 Hz, 1H), 7.10–7.56(m, 10H).

(3) Preparation of 2,2-diphenyl-1-(diphenylphosphino)-1-methylcyclopropane

Under a nitrogen atmosphere, 1-bromo-2,2-diphenylcyclopropane (1.44 g, 5.0 mmol) and magnesium (0.134 g, 5.5 mmol) and THF (10 ml) were placed in a reaction flask. Then, a trace amount of iodine was added and the mixture was stirred at 40° C. for 2 hours. After cooling, copper iodide (0.961 g, 5.0 mmol) and chlorodiphenylphosphine (0.90 ml, 5.0 mmol) were added and the resulting mixture was stirred at 40° C. for 20 hours. After cooling to room temperature, hexane (10 ml) was added to the reaction mixture, and crystal separated was then collected by filtration. The crystal was dissolved in toluene, washed with an aqueous 28% ammonia solution and a brine, and dried over anhydrous magnesium sulfate. The solvent was then removed under reduced pressure and the concentrate was recrystallized from a mixture of methanol and toluene to give the title compound (0.98 g, 50%) as white crystal.

$^1$H-NMR(CDCl$_3$) δ 1.08(d, J=2.6 Hz, 3H), 1.55(d/d, J=4.8, 9.7 Hz, 1H), 2.12(d/d, J=4.8, 15.6 Hz, 1H), 7.08–7.59 (m, 20H); $^{31}$P-NMR(CDCl$_3$) δ 8.29.

EXAMPLE 2

Preparation of 2,2-diphenyl-1-(diisopropylphosphino)-1-methylcyclopropane

Under a nitrogen atmosphere, 1-bromo-2,2-diphenylcyclopropane (1.43 g, 5.0 mmol), magnesium (0.133 g, 5.5 mmol) and THF (10 ml) were placed in a reaction flask, followed by addition of a trace amount of iodine and stirring at 40° C. for 1.5 hours. After cooling, copper iodide (0.952 g, 5.0 mmol) and chlorodiisopropylphosphine (0.80 ml, 5.0 mmol) were added and the resulting mixture was stirred at 40° C. for 5 hours, followed by cooling to room temperature. The resulting mixture was diluted with hexane (20 ml) and crystal separated was collected by filtration. The crystal was dissolved in toluene, and the toluene solution was washed with a 28% aqueous ammonia and a brine, and dried over anhydrous magnesium sulfate. Then, the solvent was removed under reduced pressure to give the title compound (1.06 g, 66%) as white crystal.

$^1$H-NMR(CDCl$_3$) δ 1.10–1.45(m, 16H), 2.20–2.46(m, 3H), 7.12–7.54(m, 10H); $^{31}$P-NMR(CDCl$_3$) δ 22.70.

EXAMPLE 3

Preparation of 2,2-diphenyl-1-(di-tert-butylphosphino)-1-methylcyclopropane

Under a nitrogen atmosphere, 1-bromo-2,2-diphenyl-cyclopropane (1.44 g, 5.0 mmol), magnesium (0.134 g, 5.5 mmol) and THF (10 ml) were placed in a reaction flask, followed by addition of a trace amount of iodine and stirring at 40° C. for one hour. After cooling, copper iodide (0.962 g, 5.0 mmol), lithium bromide (0.567 g, 6.5 mmol) and chlorodi-tert-butylphosphine (0.95 ml, 5.0 mmol) were added and the resulting mixture was stirred at 60° C. for 3 hours, followed by cooling to room temperature. The resulting mixture was diluted with hexane (20 ml) and crystal separated was collected by filtration. The crystal was dissolved in toluene, and the toluene solution was washed with a 28% aqueous ammonia and a brine, and dried over anhydrous magnesium sulfate. The solvent was then removed under reduced pressure to give the title compound (0.83 g, 47%) as white crystal.

$^1$H-NMR(CDCl$_3$) δ 1.22(d, J=11.0 Hz, 9H), 1.23–1.39(m, 1H), 1.31(d, J=10.6 Hz, 9H), 1.36(d, J=1.2 Hz, 3H), 2.27 (d/d, J=5.0, 12.6 Hz, 1H), 7.00–7.49(m, 10H); $^{31}$P-NMR (CDCl$_3$) δ 39.25.

EXAMPLE 4

Preparation of 2,2-diphenyl-1-(di-tert-butylphosphino)-1-methylcyclopropane (1) Preparation of 1-chloro-1-methyl-2,2-diphenyl-cyclopropane Under a nitrogen atmosphere, 1,1-dichloroethane (30.0 g, 303 mmol), diphenylethylene (5.59 g, 31.0 mmol) and diethyl ether (62 ml) were placed in a reaction flask and cooled to −40° C. To the mixture, n-butyllithium in hexane (45 ml, 1.56M, 70.2 mmol) was added gradually and the mixture was stirred at the same temperature for one hour, followed by warming to room temperature. Then, water was added to the reaction mixture and the organic layer was extracted with toluene. The toluene extract was dried over anhydrous magnesium sulfate and then the solvent was removed under reduced pressure. The concentrate was recrystallized from ethanol to give the title compound (5.91 g, 78%) as white crystal.

$^1$H-NMR(CDCl$_3$) δ 1.57(s, 3H), 1.67(d, J=6.2 Hz, 1H), 1.87(d, J=6.2 Hz, 1H), 7.10–7.33(m, 6H), 7.37–7.55(m, 4H).

(2) Preparation of 2,2-diphenyl-1-(di-tert-butyl-phosphino)-1-methylcyclopropane Under a nitrogen atmosphere, 1-chloro-1-methyl-2,2-diphenylcyclopropane (2.43 g, 10.0 mmol), magnesium (0.279 g, 11.5 mmol) and THF (10 ml) were placed in a reaction flask, followed by addition of a trace amount of iodine and stirring at 60° C. for 5 hours. After cooling, copper iodide (1.92 g, 10.0 mmol), lithium bromide (0.879 g, 10.1 mmol) and chlorodi-tert-butylphosphine (2.1 ml, 11.0 mmol) were added and the resulting mixture was stirred at 60° C. for 3 hours, followed by cooling to room temperature. The resulting mixture was diluted with hexane (20 ml) and crystal separated was collected by filtration. The crystal was dissolved in toluene, and the toluene solution was washed with a 28% (w/w) aqueous ammonia and a brine, and dried over anhydrous magnesium sulfate. The solvent was removed under reduced pressure to give the title compound (0.89 g, 25%) as white crystal.

EXAMPLE 5

Preparation of diphenyl(4-methoxyphenyl)amine

Under a nitrogen atmosphere, diphenylamine (0.85 g, 5.0 mmol), and biphenyl as an internal standard were placed in a reaction flask, followed by addition of 10 ml of toluene. To the mixture were added sodium tert-butoxide (0.58 g, 6.0 mmol), 4-bromoanisole (0.69 ml, 5.5 mmol), palladium acetate (2.8 mg, 0.0125 mmol) and 2,2-diphenyl-1-(di-tert-butylphosphino)-1-methylcyclopropane (8.8 mg, 0.025 mmol) obtained in Example 4 and the resulting mixture was stirred at 100° C. for 3 hours. The reaction mixture was cooled and analyzed gas chromatography to reveal the formation of the objective diphenyl(4-methoxyphenyl) amine in a yield of 95%.

$^1$H-NMR(CDCl$_3$) δ 3.80(s, 3H), 6.79–7.28(m, 14H)

EXAMPLE 6

Preparation of diphenyl(4-methoxyphenyl)amine

To a solution of diphenylamine (0.34 g, 2.0 mmol) in 4 ml of toluene were added sodium tert-butoxide (0.23 g, 2.4 mmol), 4-chloroanisole (0.27 ml, 2.2 mmol), (π-allyl)palladium chloride (3.7 mg, 0.01 mmol) and 2,2-diphenyl-1-(ditert-butylphosphino)-1-methylcyclopropane (14.1 mg, 0.04 mmol) obtained in Example 4 under a nitrogen atmosphere and the mixture was stirred for 3 hours at 100° C. The reaction mixture was cooled, washed with water, and dried over anhydrous magnesium sulfate. Then, the solvent was removed under reduced pressure, and the concentrate was purified by column chromatography to give the title compound (0.53 g, 95%) as white crystal.

EXAMPLE 7

Preparation of N-phenylcarbazole

To a solution of carbazole (0.34 g, 2.0 mmol) in xylene (4 ml) were added sodium tert-butoxide (0.23 g, 2.4 mmol), bromobenzene (0.23 ml, 2.2 mmol), palladium acetate (4.5 mg, 0.02 mmol) and 2,2-diphenyl-1-(di-tert-butylphosphino)-1-methylcyclopropane (14.1 mg, 0.04 mmol) obtained in Example 4 under a nitrogen atmosphere and the mixture was stirred for 3 hours at 120° C. The reaction mixture was cooled, washed with water, and dried over anhydrous magnesium sulfate. Then, the solvent was removed under reduced pressure, and the concentrate was purified by column chromatography to give N-phenylcarbazole (0.479 g, 98%, purity: >99%) as white crystal.

$^1$H-NMR(CDCl$_3$) δ 7.23–7.67(m, 11H), 8.15(br-d, J=7.6 Hz, 2H).

EXAMPLE 8

Preparation of 4-methoxybiphenyl

Under a nitrogen atmosphere, 4-trifluoromethane-sulfonyloxyanisole (0.49 g, 1.9 mmol), phenylboronic acid (0.29 g, 2.4 mmol), potassium fluoride (0.24 g, 4.2 mmol), (π-allyl)palladium chloride (3.6 mg, 0.01 mmol), 2,2-diphenyl-1-(di-tert-butylphosphino)-1-methylcyclopropane (14.0 mg, 0.04 mmol) obtained in Example 4 and toluene (4 ml) were placed in a reaction flask and stirred for 1.5 hours at 80° C. The reaction mixture was cooled, washed with water, and dried over anhydrous magnesium sulfate. Then, the solvent was removed under reduced pressure, and the concentrate was purified by column chromatography to give the title compound (0.34 g, 96%) as white crystal.

$^1$H-NMR(CDCl$_3$) δ 3.85(s, 3H), 6.93–7.04(m, 2H), 7.23–7.69(m, 7H).

EXAMPLE 9

Preparation of 4-methoxybiphenyl

Under a nitrogen atmosphere, 4-chloroanisole (0.30 g, 2.1 mmol), phenylboronic acid (0.37 g, 3.0 mmol), potassium phosphate n-hydrate (0.85 g), (π-allyl)palladium chloride (3.7 mg, 0.01 mmol), 2,2-diphenyl-1-(di-tert-butylphosphino)-1-methylcyclopropane (14.1 mg, 0.04 mmol) obtained in Example 4 and toluene (4 ml) were placed in a reaction flask and stirred for 3 hours at 80° C. The reaction mixture was cooled, washed with water, and dried over anhydrous magnesium sulfate. Then, the solvent was removed under reduced pressure, and the concentrate was purified by column chromatography to give the title compound (0.35 g, 90%) as white crystal.

EXAMPLE 10

Preparation of [2,2-diphenyl-1-(d-tert-butylphosphino)-1-methylcyclopropane](π-allyl)palladium chloride Under a nitrogen atmosphere, (π-allyl)palladium chloride dimer (0.183 g, 0.5 mmol), 2,2-diphenyl-1-(di-tert-butylphosphino)-1-methylcyclopropane (0.352, 1.0 mmol) and 3 ml of toluene were placed in a reaction flask and the mixture was stirred at room temperature for 6 hours. Crystal separated was filtered and dried to give the title compound (0.490 g, 91%).

$^1$H-NMR(CDCl$_3$) δ 1.01–1.16(m, 1H), 1.34–1.71(m, 10H), 1.43(d, J=5.2 Hz, 3H), 1.47(d, J=12.8 Hz, OH), 2.28–3.10(m, 1H), 3.35(br-s, 1H), 3.96(br-d, J=16.4 Hz, 1H), 4.35(br-s, 1H), 5.26(br-s, 1H), 6.92–7.06(m, 1H), 7.08–7.47(m, 7H), 7.68–7.84(m, 2H); $^{31}$P-NMR(CDCl$_3$) δ 75.63.

INDUSTRIAL APPLICABILITY

The phosphine compounds of the present invention form, with palladium compounds, palladium-phosphine complexes which show high efficiency as catalyst for the coupling reactions of unsaturated compounds and aromatic compounds.

The invention claimed is:

1. A phosphine compound of formula (1),

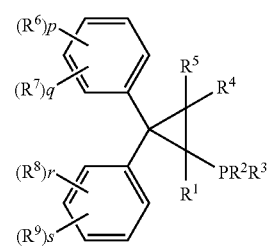

(1)

wherein $R^1$ is a hydrogen atom, an alkyl group, a cycloalkyl group or a phenyl group which may be substituted; $R^2$ and $R^3$ are each, the same or different, an alkyl group, a cycloalkyl group or a phenyl group which may be substituted; $R^4$ and $R^5$ are each, the same or different, a hydrogen atom, an alkyl group, a cycloalkyl group or a phenyl group which may be substituted; $R^6$, $R^7$, $R^8$ and $R^9$ are each, the same or different, an alkyl group, a cycloalkyl group, a phenyl group which may be substituted, an alkoxyl group, a dialkylamino group, a halogen atom, a benzyl group, a naphthyl group or a halogenated alkyl group; $R^6$ and $R^7$, or $R^8$ and $R^9$ each may be combined to form, a fused ring, a trimethylene group, a tetramethylene group or a methylenedioxy group; p, q, r and s are each an integer of from 0 to 5; and p+q, and r+s are each in the range of from 0 to 5.

2. A palladium-phosphine complex which can be obtained by reacting the phosphine compound of claim 1 with a palladium compound.

3. The palladium-phosphine complex of claim 2, wherein the palladium compound is a palladium salt or a palladium complex in which the valency of palladium is 4, 2 or 0.

4. A method of manufacturing an unsaturated compound or an aromatic compound which comprises reacting a compound of formula (3) or (4) below:

$Ar^1(X^1)_{m^1}$ (3)

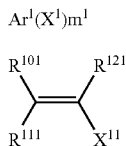
(4)

wherein, in formula (3), $Ar^1$ is an aryl group which may be substituted or a heteroaryl group which may be substituted; $X^1$ is a chlorine atom, a bromine atom, an iodine atom, a trifluoromethanesulfonyloxy group, a methanesulfonyloxy group or a para-toluenesulfonyloxy group and $m^1$ is an integer of 1 to 4, and, in formula (4), $R^{101}$, $R^{111}$ and $R^{121}$ are each, the same or different, a hydrogen atom, an alkyl group, an aryl group which may be substituted, a heteroaryl group which may be substituted, an alkoxycarbonyl group or a cyano group; $X^{11}$ is a chlorine atom, a bromine atom, an iodine atom, a trifluoromethanesulfonyloxy group, a methanesulfonyloxy group or a para-toluenesulfonyloxy group, with a compound, of formula (5) or (6) below, $Ar^2X^2$ (5)

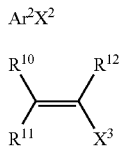
(6)

wherein, in formula (5), $Ar^2$ is an aryl group which may be substituted or a heteroaryl group which may be substituted; $X^2$ is $B(OR^{13})(OR^{14})$, $Sn(R^{15})_3$, $MgX$, $ZnX$, $Al(R^{15})_2$ or $Li$, and, in formula (6), $R^{10}$, $R^{11}$ and $R^{12}$ are each, the same or different, a hydrogen atom, an alkyl group, an aryl group which may be substituted, a heteroaryl group which may be substituted, an alkoxycarbonyl group or a cyano group; $R^{10}$ and $R^{12}$ may be combined to form a single bond, forming together with the existing double bond a triple bond; $X^3$ is a hydrogen atom, $B(OR^{13})(OR^{14})$, $Sn(R^{15})_3$, $MgX$, $ZnX$, $Al(R^{15})_2$ or $Li$; $R^{13}$ and $R^{14}$ are each, the same or different, a hydrogen atom, an alkyl group, or, combined to form an ethylene group or a 1,2-dimethylethylene group; $R^{15}$ is an alkyl group, and X is a chlorine atom, a bromine atom or an iodine atom, to give a compound of formula (7), (8), (9) or (10), $Ar^1—(Ar^2)_{m^2}$ (7)

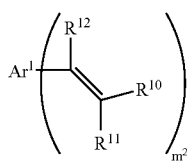
(8)

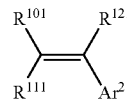
(9)

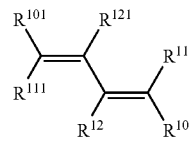
(10)

$Ar^1(X^1)_{m^1}$ (3)

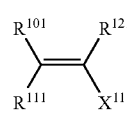
(4)

wherein $Ar^1$, $Ar^2$, $R^{10}$, $R^{11}$, $R^{11}$, $R^{12}$, $R^{101}$, $R^{111}$ and $R^{121}$ are as defined above and $m^2$ is an integer of 1 to 4, and wherein the reaction is conducted in the presence of the palladium-phosphine complex of claim 2 as a catalyst.

5. A method of manufacturing an unsaturated compound or an aromatic compound which comprises reacting a compound of formula (3) or (4) below:

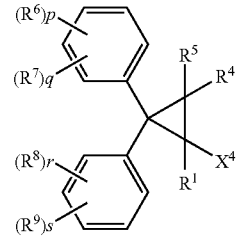
(2)

wherein, in formula (3), $Ar^1$ is an aryl group which may be substituted or a heteroaryl group which may be substituted; $X^1$ is a chlorine atom, a bromine atom, an iodine atom, a trifluoromethanesulfonyloxy group, a methanesulfonyloxy group or a para-toluenesulfonyloxy group and $m^1$ is an integer of 1 to 4, and, in formula (4), $R^{101}$, $R^{111}$ and $R^{121}$ are each, the same or different, a hydrogen atom, an alkyl group, an aryl group which may be substituted, a heteroaryl group which may be substituted, an alkoxycarbonyl group or a cyano group; $X^{11}$ is a chlorine atom, a bromine atom, an iodine atom, a trifluoromethanesulfonyloxy group, a methanesulfonyloxy group or a para-toluenesulfonyloxy group, with a compound, of formula (5) or (6) below, $Ar^2X^2$ (5)

-continued

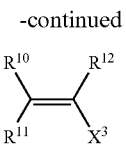 (6)

wherein, in formula (5), $Ar^2$ is an aryl group which may be substituted or a heteroaryl group which may be substituted; $X^2$ is $B(OR^{13})(OR^{14})$, $Sn(R^{15})_3$, MgX, ZnX, $Al(R^{15})_2$ or Li, and, in formula (6), $R^{10}$, $R^{11}$ and $R^{12}$ are each, the same or different, a hydrogen atom, an alkyl group, an aryl group which may be substituted, a heteroaryl group which may be substituted, an alkoxycarbonyl group or a cyano group; $R^{10}$ and $R^{12}$ may be combined to form a single bond, forming together with the existing double bond a triple bond: $X^3$ is a hydrogen atom, $B(OR^{13})(OR^{14})$, $Sn(R^{15})_3$, MgX, ZnX, $Al(R^{15})_2$ or Li; $R^{13}$ and $R^{14}$ are each, the same or different, a hydrogen atom, an alkyl group, or, combined to form an ethylene group or a 1,2-dimethylethylene group; $R^{15}$ is an alkyl group, and X is a chlorine atom, a bromine atom or an iodine atom, to give a compound of formula (7), (8), (9) or (10),

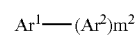 (7)

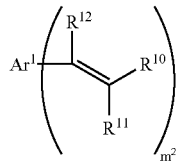 (8)

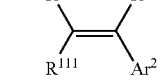 (9)

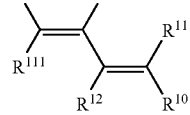 (10)

wherein $Ar^1$, $Ar^2$, $R^{10}$, $R^{11}$, $R^{12}$, $R^{101}$, $R^{111}$ and $R^{121}$ are as defined above and $m^2$ is an integer of 1 to 4, and wherein the reaction is conducted in the presence of the phosphine compound of claim 1 and a palladium compound as catalysts.

6. A method of manufacturing an unsaturated compound or an aromatic compound, which comprises reacting a compound of formula (3) or (4) below,

 (3)

-continued

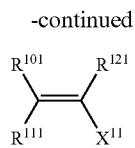 (4)

wherein, in formula (3), $Ar^1$ is an aryl group which may be substituted or a heteroaryl group which may be substituted; $X^1$ is a chlorine atom, a bromine atom, an iodine atom, a trifluoromethanesulfonyloxy group, a methanesulfonyloxy group or a para-toluenesulfonyloxy group and $m^1$ is an integer of from 1 to 4, and, in formula (4), $R^{101}$, $R^{111}$ and $R^{121}$ are each, the same or different, a hydrogen atom, an alkyl group, an aryl group which may be substituted, a heteroaryl group which may be substituted, an alkoxycarbonyl group or a cyano group; $X^{11}$ is a chlorine atom, a bromine atom, an iodine atom, a trifluoromethanesulfonyloxy group, a methanesulfonyloxy group or a para-toluenesulfonyloxy group, with an oxygen compound or a nitrogen compound of formula (11) below, $$R^{16}\text{-QH} \quad (11)$$

wherein $R^{16}$ is an alkyl group, an aryl group which may be substituted or a heteroaryl group which may be substituted; Q is an oxygen atom,

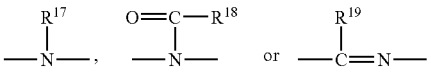

wherein $R^{17}$, $R^{18}$ and $R^{19}$ are each a hydrogen atom, an alkyl group, an aryl group which may be substituted or a heteroaryl group which may be substituted; and $R^{16}$ and $R^{17}$ may be combined to form a divalent aromatic ring which may be substituted, to give a compound of formula (12) or (13) below,

 (12)

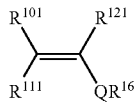 (13)

wherein $Ar^1$, Q, $R^{16}$, $R^{101}$, $R^{111}$ and $R^{121}$ are as defined above and $m^3$ is an integer of 1 to 4, and wherein the reaction is conducted in the presence of the palladium-phosphine complex of claim 2 as a catalyst.

7. A method of manufacturing an unsaturated compound or an aromatic compound which comprises reacting an aromatic compound of formula (3),

 (3)

wherein $Ar^1$ is an aryl group which may be substituted or a heteroaryl group which may be substituted; $X^1$ is a chlorine atom, a bromine atom, an iodine atom, a trifluoromethanesulfonyloxy group, a methanesulfonyloxy group or a para-toluenesulfonyloxy group, and $m^1$ is an integer of from 1 to 4, with a carbonyl compound or a cyano compound of formula (14),

wherein $R^{18}$ is a hydrogen atom, $CO_2R^{20}$, $C(=O)R^{21}$ or a cyano group; $R^{19}$ is $CO_2R^{22}$, $C(=O)R^{23}$ or a cyano group; $R^{20}$, $R^{21}$, $R^{22}$ and $R^{23}$ are each an alkyl group, an aryl group which may be substituted or a heteroaryl group which may be substituted, to give a compound of formula (15),

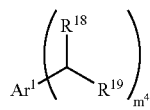

wherein $Ar^1$, $R^{18}$ and $R^{19}$ are as defined above and $m^4$ is an integer of 1 to 4, and wherein the reaction is conducted in the presence of the palladium-phosphine complex of claim 2 as a catalyst.

8. A method of manufacturing an unsaturated compound or an aromatic compound which comprises reacting an aromatic compound of formula (3),

wherein $Ar^1$ is an aryl group which may be substituted or a heteroaryl group which may be substituted; $X^1$ is a chlorine atom, a bromine atom, an iodine atom, a trifluoromethanesulfonyloxy group, a methanesulfonyloxy group or a para-toluenesulfonyloxy group; and $m^1$ is an integer of from 1 to 4, with carbon monoxide and an alcohol of formula (16),

wherein $R^{24}$ is an alkyl group,
to give a carboxylic ester of formula (17),

wherein $Ar^1$ and $R^{24}$ are as defined above and $m^5$ is an integer of 1 to 4, and wherein the reaction is conducted in the presence of the palladium-phosphine complex of claim 2 as a catalyst.

9. The method of manufacturing an unsaturated compound, as in claim 4, which comprises carrying out the reaction in the presence of a base.

10. A method of manufacturing an unsaturated compound or an aromatic compound which comprises reacting a compound of formula (3) or (4) below, $$Ar^1(X^1)_{m^1} \quad (3)$$

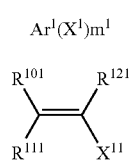

wherein, in formula (3), $Ar^1$ is an aryl group which may be substituted or a heteroaryl group which may be substituted; $X^1$ is a chlorine atom, a bromine atom, an iodine atom, a trifluoromethanesulfonyloxy group, a methanesulfonyloxy group or a para-toluenesulfonyloxy group and $m^1$ is an integer of from 1 to 4, and, in formula (4), $R^{101}$, $R^{111}$ and $R^{121}$ are each, the same or different, a hydrogen atom, an alkyl group, an aryl group which may be substituted, a heteroaryl group which may be substituted, an alkoxycarbonyl group or a cyano group; $X^{11}$ is a chlorine atom, a bromine atom, an iodine atom, a trifluoromethanesulfonyloxy group, a methanesulfonyloxy group or a para-toluenesulfonyloxy group, with an oxygen compound or a nitrogen compound of formula (11) below,

wherein $R^{16}$ is an alkyl group, an aryl group which may be substituted or a heteroaryl group which may be substituted; Q is an oxygen atom,

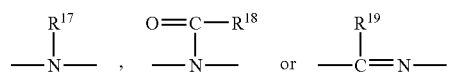

wherein $R^{17}$, $R^{18}$ and $R^{19}$ are each a hydrogen atom, an alkyl group, an aryl group which may be substituted or a heteroaryl group which may be substituted; and $R^{16}$ and $R^{17}$ may be combined to form a divalent aromatic ring which may be substituted, to give a compound of formula (12) or (13) below,

wherein $Ar^1$, Q, $R^{16}$, $R^{101}$, $R^{111}$ and $R^{121}$ are as defined above and $m^3$ is an integer of 1 to 4, and wherein the reaction is conducted in the presence of the phosphine compound of claim 1 and a palladium compound as catalysts.

11. A method of manufacturing an unsaturated compound or an aromatic compound which comprises reacting an aromatic compound of formula (3),

wherein $Ar^1$ is an aryl group which may be substituted or a heteroaryl group which may be substituted; $X^1$ is a chlorine atom, a bromine atom, an iodine atom, a trifluoromethanesulfonyloxy group, a methanesulfonyloxy group or a para-toluenesulfonyloxy group, and $m^1$ is an integer of from 1 to 4, with a carbonyl compound or a cyano compound of formula (14),

wherein $R^{18}$ is a hydrogen atom, $CO_2R^{20}$, $C(=O)R^{21}$ or a cyano group; $R^{19}$ is $CO_2R^{22}$, $C(=O)R^{23}$ or a cyano group; $R^{20}$, $R^{21}$, $R^{22}$ and $R^{23}$ are each an alkyl group, an aryl group which may be substituted or a heteroaryl group which may be substituted, to give a compound of formula (15),

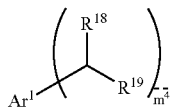

wherein $Ar^1$, $R^{18}$ and $R^{19}$ are as defined above and $m^4$ is an integer of 1 to 4, and wherein the reaction is conducted in the presence of the phosphine compound of claim 1 and a palladium compound as catalysts.

12. A method of manufacturing an unsaturated compound or an aromatic compound which comprises reacting an aromatic compound of formula (3), $$Ar^1(X^1)_{m^1} \quad (3)$$

wherein $Ar^1$ is an aryl group which may be substituted or a heteroaryl group which may be substituted; $X^1$ is a chlorine atom, a bromine atom, an iodine atom, a trifluoromethanesulfonyloxy group, a methanesulfonyloxy group or a para-toluenesulfonyloxy group; and $m^1$ is an integer of from 1 to 4, with carbon monoxide and an alcohol of formula (16), $$R^{24}OH \quad (16)$$

wherein $R^{24}$ is an alkyl group, to give a carboxylic ester of formula (17), $$Ar^1(CO_2R^{24})m^5 \quad (17)$$

wherein $Ar^1$ and $R^{24}$ are as defined above and m5 is an integer of 1 to 4, and wherein the reaction is conducted in the presence of the phosphine compound of claim 1 and a palladium compound as catalysts.

* * * * *